US00PP34645P3

(12) United States Plant Patent
Schoone

(10) Patent No.: US PP34,645 P3
(45) Date of Patent: Oct. 11, 2022

(54) **X *DORITAENOPSIS* PLANT NAMED 'BULLS EYE'**

(50) Latin Name: **x *Doritaenopsis (Doritis* x *Phalaenopsis)***
Varietal Denomination: Bulls Eye

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 17/666,080

(22) Filed: Feb. 7, 2022

(65) Prior Publication Data

US 2022/0256754 P1 Aug. 11, 2022

Related U.S. Application Data

(60) Provisional application No. 63/148,076, filed on Feb. 10, 2021.

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ..... A01H 5/02; A01H 5/00; A01H 6/62
See application file for complete search history.

(56) References Cited

PUBLICATIONS

CPVO Register 4.1.50 for *Phalaenopsis* Bulls Eye retrieved on Apr. 27, 2022 at https://online.plantvarieties.eu/publicConsultationDetails?registerId=20210823&denomination=bulls%20eye, 3 pp. (Year: 2022).*
Orchid Web Phal. Fancy Fire, retrieved on Apr. 27, 2022 at https://www.orchidweb.com/orchids/phalaenopsis/hybrids/phal-fancy-fire, 3 pp. (Year: 2022).*

* cited by examiner

*Primary Examiner* — June Hwu
(74) *Attorney, Agent, or Firm* — C. Anne Whealy

(57) ABSTRACT

A new and distinct cultivar of *Doritaenopsis* plant named 'Bulls Eye', characterized by its upright plant habit; moderately vigorous growth habit; strong, long and narrow leaves; freely flowering habit; dark purplish red-colored flowers with purple-colored labellum; and good postproduction longevity.

2 Drawing Sheets

Figure 1:
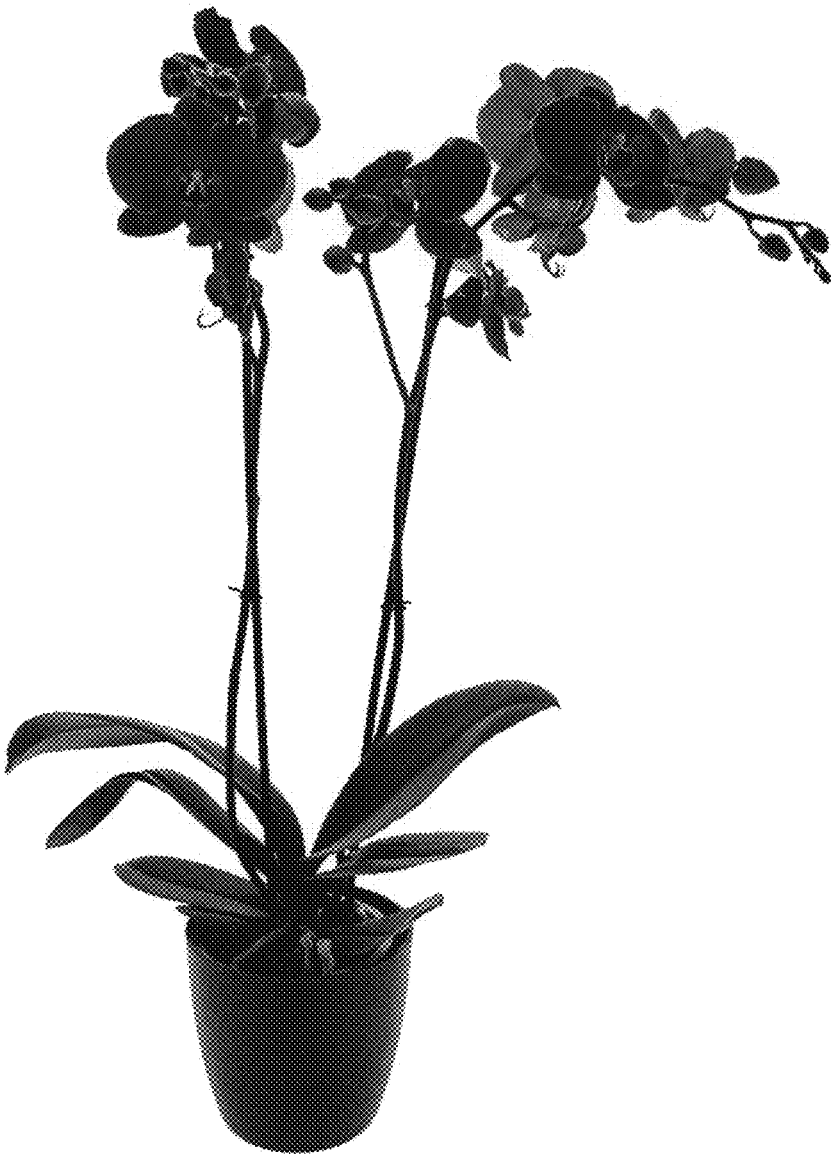

Botanical designation: x *Doritaenopsis* (*Doritis* x *Phalaenopsis*).
Cultivar denomination: 'BULLS EYE'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Floricultura B.V. of Heemskerk, The Netherlands on Mar. 18, 2021, application number 2021/0823. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of x *Doritaenopsis* plant, botanically known as x *Doritaenopsis* (*Doritis* x *Phalaenopsis*), commonly referred to as *Doritaenopsis* and hereinafter referred to by the name 'Bulls Eye'.

The new *Doritaenopsis* plant is a product of a planned breeding program conducted by the Inventor in Yünlin, Taiwan and Heemskerk, The Netherlands. The objective of the breeding program is to develop new fast-growing and freely flowering *Doritaenopsis* plants with good leaf shape and flowers with unique and attractive patterns and coloration.

The new *Doritaenopsis* plant originated from a cross-pollination on Apr. 22, 2014 in Yünlin, Taiwan of *Doritis hybrida* 'KLINGLM140' (trade name, Elegant Wibi Soerjadi), not patented, as the female, or seed, parent with *Phalaenopsis hybrida* 'Red Dragon', not patented, as the male, or pollen, parent. The new *Doritaenopsis* plant was discovered and selected by the Inventor as a single flowering plant from within the progeny of the stated cross-pollination grown in a controlled greenhouse environment in Heemskerk, The Netherlands in August, 2018.

Asexual reproduction of the new *Doritaenopsis* plant by in vitro meristem propagation in a controlled environment in Assendelft, The Netherlands since August, 2019 has shown that the unique features of this new *Doritaenopsis* plant are stable and reproduced true to type in successive generations.

SUMMARY OF THE INVENTION

Plants of the new *Doritaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Bulls Eye'. These characteristics in combination distinguish 'Bulls Eye' as a new and distinct *Doritaenopsis* plant:

1. Upright plant habit.
2. Moderately vigorous growth habit.
3. Strong, long and narrow leaves.
4. Freely flowering habit.
5. Dark purplish red-colored flowers with purple-colored labellum.
6. Good postproduction longevity.

Plants of the new *Doritaenopsis* can be compared to plants of the female parent, 'KLINGLM140'. Plants of the new *Doritaenopsis* differ primarily from plants of 'KLINGLM140' in flower color as plants of the new *Doritaenopsis* have dark purplish red-colored flowers whereas plants of 'KLINGLM140' have white-colored flowers.

Plants of the new *Doritaenopsis* can be compared to plants of the male parent, 'Red Dragon'. Plants of the new *Doritaenopsis* differ primarily from plants of 'Red Dragon' in flower color as plants of the new *Doritaenopsis* have dark purplish red-colored flowers whereas plants of 'Red Dragon' have red-colored flowers.

Plants of the new *Doritaenopsis* can be compared to plants of *Phalaenopsis hybrida* 'Fancy Fire', not patented. In side-by-side comparisons, plants of the new *Doritaenopsis* differ primarily from plants of 'Fancy Fire' in labellum color as plants of the new *Doritaenopsis* have purple-colored labellum whereas plants of 'Fancy Fire' have white, yellow, violet and orangish red-colored labellum. In addition, the white-colored petal margin edges of the new *Doritaenopsis* are narrower than the petal margin edges of 'Fancy Fire'.

BRIEF DESCRIPTION OF THE PHOTOGRAPHS

The accompanying photographs illustrate the overall appearance of the new *Doritaenopsis* plant showing the colors as true as it is reasonably possible to obtain in colored reproductions of this type. Colors in the photographs may differ slightly from the color values cited in the detailed botanical description which accurately describe the colors of the new *Doritaenopsis* plant.

The photograph on the first sheet (FIG. 1) is a side perspective view of a typical flowering plant of 'Bulls Eye' grown in a container.

Figure 2:
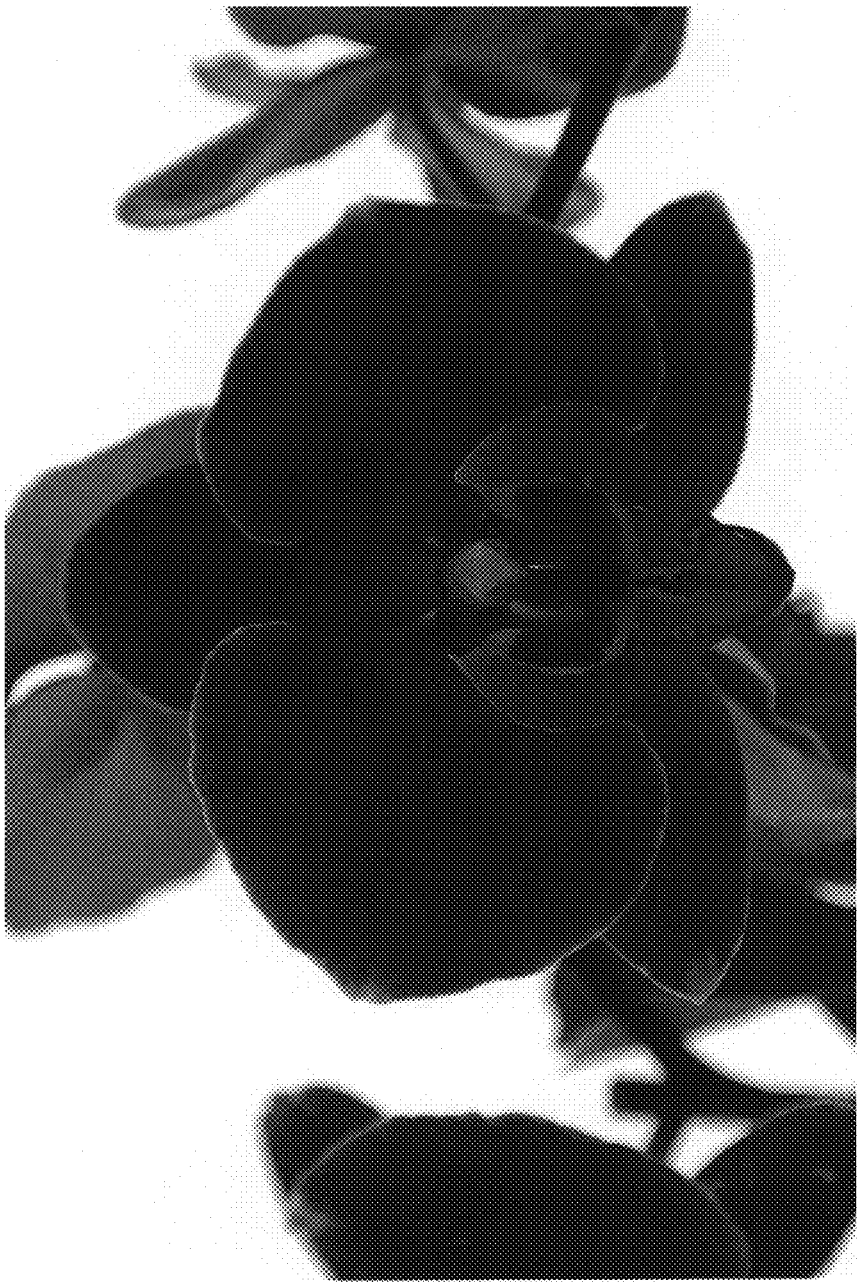

The photograph on the second sheet (FIG. 2) is a close-up view of a typical flower of 'Bulls Eye'.

DETAILED BOTANICAL DESCRIPTION

The aforementioned photographs and following observations and measurements describe plants grown during the spring and early summer in 10.5-cm containers in a glass-covered greenhouse in Heemskerk, The Netherlands and under cultural practices typically used in commercial *Doritaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the 18 months of production, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: X *Doritaenopsis* (*Doritis* x *Phalaenopsis*) 'Bulls Eye'.

Parentage:

*Female parent.*—*Doritis hybrida* 'KLINGLM140', not patented.

*Male parent.*—*Phalaenopsis hybrida* 'Red Dragon', not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Fine, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically two inflorescences per plant, each inflorescence with numerous flowers; monopodial; moderately vigorous growth habit and moderate growth rate.

*Plant height, substrate level to top of foliar plane.*—About 16.8 cm.

*Plant height, substrate level to top of inflorescences.*—About 49.4 cm.

*Plant diameter or spread.*—About 36.6 cm.

Leaf description:

*Arrangement and quantity.*—Distichous, simple; sessile; about six leaves per plant.

*Length.*—About 20.4 cm.

*Width.*—About 6.8 cm.

*Aspect.*—Outwardly arching.

*Shape.*—Oblanceolate to narrowly elliptic; slightly carinate.

*Apex.*—Unequal acute.

*Base.*—Sheathing. Sheath length: About 2.1 cm. Sheath width: About 1.3 cm. Sheath color: Close to 143B and towards the apical margin, close to 143A.

*Margin.*—Entire.

*Texture and luster, upper and lower surfaces.*—Smooth, glabrous; moderately glossy.

*Venation pattern.*—Camptodromous.

*Color.*—Developing leaves, upper surface: Slightly darker than a blend of NN137A and 147A. Developing leaves, lower surface: Close to 146A; margin edges tinged with close to 200A. Fully expanded leaves, upper surface: Darker than a blend of NN137A and 147A; venation, close to 139A. Fully expanded leaves, lower surface: Close to 146A; margin edges, close to NN137B; venation, close to NN137B.

Inflorescence description:

*Appearance and flowering habit.*—Showy zygomorphic flowers arranged on axillary branched racemes; typically two inflorescences per plant; each inflorescence with about 16 flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about eight weeks on the plant; flowers not persistent.

*Inflorescence length* (*lowermost flower to inflorescence apex*).—About 31.3 cm.

*Inflorescence width*.—About 15.2 cm.

*Flower buds*.—Height: About 1.9 cm. Diameter: About 1.3 cm by 1.6 cm. Shape: Broadly ovate. Color: Close to 146D; towards the apex, strongly tinged with close to 183A.

*Flower size*.—About 7.7 cm (vertical) by 8.1 cm (horizontal).

*Flower depth*.—About 5.1 cm.

*Petals, quantity and arrangement*.—Three, two lateral petals and one center petal transformed into a labellum.

*Lateral petals*.—Length: About 4 cm. Width: About 4.65 cm. Shape: Reniform. Apex: Retuse. Margin: Entire; distally, occasionally with a shallow incision. Texture and luster, upper and lower surfaces: Smooth, glabrous, velvety; matte. Color: When opening, upper surface: Close to 187A; margin edges, close to N155A tinged with close to N78A. When opening, lower surface: Close to 196C; towards the margins, tinged with close to N77D; venation, slightly lighter than N77D. Fully opened, upper surface: Close to a blend of N186D and 187C; towards the apex and margins, close to N79C; margin edges, close to 155A; venation, similar to lamina colors; color does not change with subsequent development. Fully opened, lower surface: Close to 76C; venation, close to 77C; color does not change with subsequent development.

*Labella*.—Appearance: Three-parted with two lateral lobes and a central lobe. Length, lateral lobes: About 2.2 cm. Width, lateral lobes: About 1.5 cm. Length, central lobe: About 3.4 cm. Width, central lobe: About 0.5 cm to 2.2 cm. Shape, lateral lobes: Obovate; slightly convex. Shape, central lobe: Deltoid. Apex, lateral lobes: Obtuse. Apex, central lobe: Elongated and cleft with cirrhose apices, about 1.5 cm in length and about 8 mm in width. Margins, lateral and central lobes: Entire. Texture and luster, upper and lower surfaces: Smooth, glabrous, moderately velvety; matte. Callosities: Located at the base of the labellum and attachment point of the lateral petals; about 4 mm in length, about 6 mm in width and about 6 mm in height. Color: When opening, upper surface: Lateral lobes: Close to N78A; towards the base, close to 187B; margin edges, close to N78D to lighter than N78D. Central lobe: Close to N78B; towards the base of the wide part, close to 70A; wide part, dotted and blotched with close to 4C and 183A; cirrhose apices and main vein, close to a blend of N79B and N79C; towards the base at the column connection, close to 178A to 178B and at the column connection, close to 155C. Callosities: Close to 178A. When opening, lower surface: Lateral lobes: Close to N78A; at the base, close to 196C. Central lobe: Close to N78A; wide part, close to a blend of 70A and 71A and towards the center, close to N74D; at the base (at column connection), close to 196B to 196C. Callosities: Close to 4A; towards the base, close to 155C. Fully opened, upper surface: Lateral lobes: Close to N78A; towards the base, close to N79C and at the base, close to a blend of 183A and 187C dotted and blotched with close to 11A and 183A; margin edges, close to 77D to lighter than 77D. Central lobe: Close to a blend of N78A and N78B; towards the base of the wide part, close to 71A to 71B; wide part, dotted and blotched with close to 11A and 183A; cirrhose apices and main vein, close to a blend of N79B and N79C; towards the base at the column connection, close to 178A to 178B and at the column connection, close to 76C. Callosities: Close to 183B. Fully opened, lower surface: Lateral lobes: Close to N78A; at the base, close to 196D slightly tinged with close to 160A. Central lobe: Close to N78A; wide part, close to 187C and towards the center, close to N74D; at the base (at column connection), close to 198D; margin edges, close to 187A. Callosities: Close to 4A; towards the base, close to 4C.

*Sepals*.—Quantity and arrangement: Three, one upper dorsal sepal and two lower lateral sepals. Length, dorsal sepal: About 4 cm. Width, dorsal sepal: About 2.65 cm. Length, lateral sepals: About 4.4 cm. Width, lateral sepals: About 2.55 cm. Shape, dorsal sepal: Broadly elliptic. Shape, lateral sepals: Broadly ovate. Apex, dorsal sepal: Retuse to obtuse. Apex, lateral sepals: Bluntly acute. Base, dorsal sepal: Truncate. Base, lateral sepals: Cuneate. Margin, dorsal sepal: Entire. Margin, lateral sepals: Entire; lower margin, coarsely undulate. Texture and luster, all sepals, upper and lower surfaces: Smooth, glabrous, velvety; matte. Color, dorsal sepal: When opening, upper surface: Close to 187A; apical narrow margin edges, close to N155A tinged with close to N78A. When opening, lower surface: Close to 146D; towards the margins, close to 186D. Fully opened, upper surface: Close to a blend of N186D and 187D; towards the margins and apex, close to N78A; narrow margin edges, close to N155A. Fully opened, lower surface: Close to 169C; towards the apex, tinged with close to 75B; venation, close to 75A. Color, lateral sepals: When opening, upper surface: Close to 187A; apical narrow margin edges, close to N155A tinged with close to N78A. When opening, lower surface: Close to 146D; towards the apex, tinged with close to 184C. Fully opened, upper surface: Close to a blend of N186D and 187D; towards the margins and apex, close to N78A; narrow margin edges, close to N155A. Fully opened, lower surface: Close to 193A; towards the margins and apex, tinged with close to 72B.

*Peduncles*.—Length: About 63.2 cm. Diameter: About 5 mm. Strength: Strong. Aspect: Upright to outwardly arching. Texture and luster: Smooth, glabrous; matte. Color: Close to 138C densely covered with fine dots, darker than a blend of 147A and N199A.

*Pedicels*.—Length: About 3.4 cm. Diameter: About 3.5 mm. Strength: Moderately strong. Aspect: About 65° from peduncle axis. Texture and luster: Smooth, glabrous; matte. Color: Proximally, close to a blend of 147A and 148A; distally, close to 157D; lower surface, close to 145A and distally, close to 157D.

*Reproductive organs*.—Androecium: Column length: About 9 mm. Column width: About 6 mm. Column color: Close to NN78B. Pollinia quantity: Two. Pollinia diameter (per two pollinia): About 2.5 mm. Pollinia color: Close to 23A. Gynoecium: Stigma length: About 4 mm. Stigma width: About 4.5 mm. Stigma shape: Reniform. Stigma color: Close to NN155C. Ovary length: About 7 mm. Ovary diameter: About 1 mm. Ovary color: Close to 150C. Seeds and fruits: To date, seed and fruit development have not been observed on plants of the new *Doritaenopsis*.

Pathogen & pest resistance: To date, plants of the new *Doritaenopsis* have not been shown to be resistant to pathogens and pests common to *Doritaenopsis* plants.

Temperature tolerance: Plants of the new *Doritaenopsis* have been observed to tolerate high temperatures to about 40° C. and are suitable for USDA Hardiness Zones 10 to 12.

It is claimed:

1. A new and distinct *Doritaenopsis* plant named 'Bulls Eye' as illustrated and described.

* * * * *